United States Patent
Wang

(10) Patent No.: US 12,008,754 B2
(45) Date of Patent: Jun. 11, 2024

(54) IMAGE RECOGNITION BASED WORKSTATION FOR EVALUATION ON QUALITY CHECK OF COLONOSCOPY

(71) Applicant: Tianjin Yujin Artificial Intelligence Medical Technology Co., Ltd., Tianjin (CN)

(72) Inventor: Yufeng Wang, Tianjin (CN)

(*) Notice: Subject to any disclaimer, the term of this patent is extended or adjusted under 35 U.S.C. 154(b) by 342 days.

(21) Appl. No.: 17/605,250

(22) PCT Filed: Apr. 9, 2020

(86) PCT No.: PCT/CN2020/000061
§ 371 (c)(1),
(2) Date: Oct. 21, 2021

(87) PCT Pub. No.: WO2020/215805
PCT Pub. Date: Oct. 29, 2020

(65) Prior Publication Data
US 2022/0198660 A1   Jun. 23, 2022

(30) Foreign Application Priority Data
Apr. 25, 2019 (CN) .......................... 201910339987.2

(51) Int. Cl.
*G06T 7/00* (2017.01)
*G16H 30/40* (2018.01)
*G16H 50/20* (2018.01)

(52) U.S. Cl.
CPC ........... *G06T 7/0012* (2013.01); *G16H 30/40* (2018.01); *G16H 50/20* (2018.01); *G06T 2207/20* (2013.01); *G06T 2207/30028* (2013.01)

(58) Field of Classification Search
CPC .............................. G06T 7/0012; G16H 50/20
See application file for complete search history.

(56) References Cited

U.S. PATENT DOCUMENTS

2013/0096424 A1* 4/2013 Xu ..................... A61B 1/00057
600/424

FOREIGN PATENT DOCUMENTS

CN          109146884       *  1/2019  ............... G06N 3/04

* cited by examiner

*Primary Examiner* — Tuan H Nguyen

(57) ABSTRACT

Disclosed is an image recognition based workstation for evaluation on quality check of colonoscopy, relating to the technical field of intelligent healthcare. The workstation comprises an algorithm module, a timing module, a data transmission module, a display device, a colonoscopy device, and a computer host. The colonoscopy device is connected with the data transmission module, and the data transmission module is connected with the computer host through the algorithm module and the timing module; and the display device is used to display the results of the computer host. The described workstation can evaluate different techniques of doctors during each colonoscopy check by means of different image recognition algorithms. During the checking process, the workstation determines whether the operation of the doctor is appropriate and gives the corresponding reference suggestions, which is responsible for patients and allows the doctor to continuously improve his ability during the checking process, thereby greatly reducing the pressure on doctors, and allowing doctors to focus more on other more creative tasks, and besides bringing huge economic and social benefits.

1 Claim, 1 Drawing Sheet

IMAGE RECOGNITION BASED WORKSTATION FOR EVALUATION ON QUALITY CHECK OF COLONOSCOPY

BACKGROUND OF THE INVENTION

The invention relates to the technical field of intelligent medical treatment, and in particular to an image recognition based workstation for evaluation on colonoscopy quality.

A colonoscope has been widely used in the diagnosis and treatment of intestinal diseases. As a safe, accurate and well-tolerated instrument, it plays an important role in both initial screening and subsequent detection of colorectal cancer (CRC). Colonoscopy is essential for early detection of precancerous lesions and prevention of the CRC, which can reduce a CRC risk by 77% as shown in studies.

However, many factors impact on quality of the colonoscopy, including three types of evaluation indexes impacting on the quality of colonoscopy: basic characteristics of patients, intestinal preparation, etc. (before the colonoscopy), a cecal insertion rate, colonoscope withdrawal time, an adenoma detection rate, etc. (during the colonoscopy), and a bleeding rate, a perforation rate, etc. (after the colonoscopy), of which factors related to a colonoscope operator (that is, during the colonoscopy are the most impactful.

Thus, it is crucial to improve quality during the colonoscopy to reduce the CRC risk, especially to reduce an incidence rate of interphase CRC. But colonoscopy doctors have different professional levels, and an examination standard of the doctors will be lowered due to exhaustion caused by multiple operations in one day, so it is urgent to develop an image recognition based workstation for evaluation on colonoscopy quality.

BRIEF SUMMARY OF THE INVENTION

The object of the present invention is to overcome the above technical defects, so as to provide an image recognition based workstation for evaluation on colonoscopy quality.

In order to achieve the above object, the present invention uses the following technical solution: the image recognition based workstation for evaluation on colonoscopy quality. The workstation includes: an algorithm module, a timing module, a data transmission module, display equipment, colonoscope equipment and a computer host, where the colonoscope equipment is connected to the data transmission module, the data transmission module is connected to the computer host by means of the algorithm module and the timing module, the display equipment is configured to display a result of the computer host, and the algorithm module includes a colonoscopy fuzzy detection algorithm, an examination completeness degree algorithm, a lesion recognition algorithm, a static detection algorithm and a wall collision detection algorithm.

A fuzzy detection algorithm uses a function in opencv to gray an input image, uses a apiece operator to detect a global variance of the whole image, and conducts marginal detection on the whole image, so that the global variance of the whole image is calculated, and an appropriate threshold value s determined so as to determine whether the image is fuzzy or not; the examination completeness degree algorithm is used to detect an average gray value of part of areas of four corners in the input image and select an appropriate threshold value to determine whether the four corners are bright or dark, and under the condition that brightness of each corner certain number of image dead angles continuously input is included, an examination is complete, and otherwise, the examination is incomplete; the lesion recognition algorithm uses a YOLO V3 algorithm, and can detect a position of a lesion in an input video image in real time; the static detection algorithm is used to calculate a gray histogram of two images spaced a certain number of frames apart, and when a matching degree reaches a certain threshold value, it is determined that a colonoscope lens is in a static state within time corresponding to the number of frames; the wall collision detection algorithm trains a collected picture that is too dose to an intestinal wall through a deep learning method, so as to obtain a detection model; and the timing module is used to calculate total examination time and colonoscope withdrawal time.

The present invention has the beneficial effects that the present invention can evaluate different methods of a doctor during colonoscopy every time by means of different image recognition algorithms, and determine whether the doctor operates properly and give a corresponding reference suggestion during the colonoscopy, and can supervise the doctor to conduct the colonoscopy more seriously so as to be responsible to a patient. Thus, an ability of the doctor during the colonoscopy can be continuously improved, pressure of the doctor can be greatly reduced, the doctor can focus on other more creative tasks, and great economic and social benefits are created.

DETAILED DESCRIPTION OF THE INVENTION

Figures 1, 2:
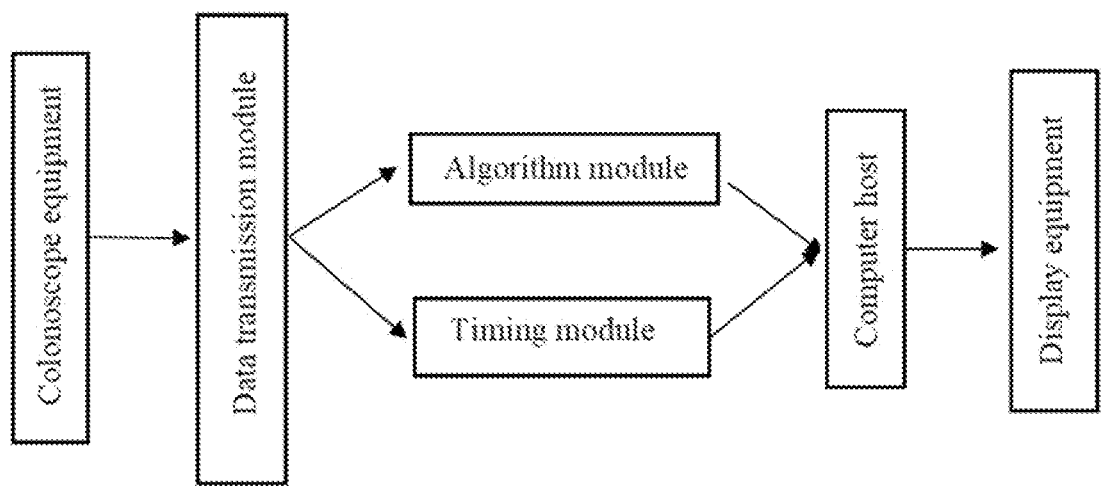
FIG. 1 is a structural schematic diagram of the present invention.
FIG. 2 is a schematic diagram of a constitution of an algorithm module in the present invention.

The specific embodiments of the present invention will be described in details below in conjunction with the accompanying drawings and the exemplary embodiments. As shown in FIG. 1, an image recognition based workstation for evaluation on colonoscopy quality of the present invention includes parts of an algorithm module, a timing module, a data transmission module, display equipment, colonoscope equipment and a computer host.

As shown in FIG. 2, the algorithm module includes a colonoscopy fuzzy detection algorithm, an examination completeness degree algorithm, a lesion recognition algorithm a static detection algorithm and a wall collision detection algorithm.

The examination completeness degree algorithm is used to count the cycle number of rotation of a lens during colonoscope withdrawal through the above method, when a visual field is static, the function is not determined, and when the cycle number of rotation reaches a certain number, it is determined that an intestinal examination by a doctor is complete. The fuzzy detection algorithm is used to calculate the number of fuzzy frames from the colonoscope withdrawal to an end through the above method, and calculate colonoscope withdrawal sharpness of the examination according to a formula: colonoscope withdrawal sharpness of the number of fuzzy frames/the number of total frames so as to determine operation of the doctor. The lesion recognition algorithm is used to recognize a lesion and mark a position thereof during the examination, and finally record the total number of lesions. The static detection algorithm is used to calculate static time from the colonoscope withdrawal to the end through the above method, and calculate effective colonoscope withdrawal time in cooperation with the timing module. The wall collision detection algorithm is used to calculate the number of frames of an image that is too close to an intestinal wall during the colonoscope withdrawal through the above method, and calculate a safety index according to a formula: safety index=1−the number of red fuzzy frames/the number of total frames.

The timing module is connected to the colonoscope equipment, and total examination time, colonoscope entering time and colonoscope withdrawal) time are calculated according to time nodes, marked by the doctor through stepping on a pedal, of entering an anus, reaching an appendix opening and exiting the anus; and by combining with the above algorithm, the effective colonoscope withdrawal time is calculated according to a formula: effective colonoscope withdrawal time (s)=colonoscope withdrawal time−(the number of static frames+the number of fuzzy frames/frame rate.

The meanings of the parameters calculated according to all the algorithms of the present invention are as follows:

Total examination time is to score an index for evaluating proficiency of the doctor; total colonoscope withdrawal time is to increase a colonoscope withdrawal speed so as to reflect efficiency of the doctor; the colonoscope withdrawal sharpness: during the colonoscope withdrawal, the higher a proportion of clear visual frames, the more effective the examination is, and the fewer omissions are; effective colonoscope withdrawal time: in unit time of effective colonoscope withdrawal movement time, a visual field is changed and clearly recognizable, the function is used to evaluate effectiveness of colonoscope withdrawal operation of the doctor and reduce invalid colonoscope withdrawal operation, and the effective colonoscope withdrawal time is monitored to avoid too long meaningless stop of the doctor, and is qualified when longer than or equal to 6 min as required by the doctor; and a safety index is to evaluate a proportion of the doctor touching the intestinal wall during the operation, and the condition that the proportion is large, the safety index is low, indicating that a risk caused by the operation of the doctor is high.

The above mentioned description is merely the preferred implementation of the present invention, it should be pointed out that those of ordinary skin in the art may also make some improvements and modifications without departing from the principle of the present invention, and these improvements and modifications should also fail within the scope of protection of the present invention.

What is claimed is:

1. An image recognition based workstation for evaluation on quality check of colonoscopy, comprising: an algorithm module, a timing module, a data transmission module, display equipment, colonoscope equipment and a computer host, wherein the colonoscope equipment is connected to the data transmission module, the data transmission module is connected to the computer host by means of the algorithm module and the timing module, the display equipment is configured to display a result of the computer host, and the algorithm module comprises a fuzzy detection algorithm, an examination completeness degree algorithm, a lesion recognition algorithm, a static detection algorithm and a wall collision detection algorithm, wherein the fuzzy detection algorithm uses a function in opencv to gray an input image to obtain a grayed input image, uses a laplace operator to detect a global variance of the grayed input image, and conducts marginal detection on the grayed input image, so that the global variance of the grayed input image is calculated, and first threshold value is determined so as to determine whether the grayed input image is fuzzy or not; the examination completeness degree algorithm is used to detect an average gray value of part of areas of four corners in the grayed input image and select second threshold value to determine whether the four corners are bright or dark, and under a condition that brightness of each corner in a certain number of image dead angles continuously input is included, an examination is complete, and otherwise, the examination is incomplete; the lesion recognition algorithm uses a YOLO V3 algorithm, and can detect a position of a lesion in an input video image in real time; the static detection algorithm is used to calculate a gray histogram of two images spaced a certain number of frames apart, and when a matching degree reaches a certain threshold value, it is determined that a colonoscope lens is in a static state within time corresponding to the number of frames; the wall collision detection algorithm trains a collected picture that is too close to an intestinal wall through a deep learning method, so as to obtain a detection model; and the timing module is used to calculate total examination time and colonoscope withdrawal time.

* * * * *